United States Patent
Ota et al.

(10) Patent No.: US 11,780,473 B2
(45) Date of Patent: Oct. 10, 2023

(54) VEHICLE CONTROLLER AND VEHICLE CONTROL SYSTEM

(71) Applicant: SUBARU CORPORATION, Tokyo (JP)

(72) Inventors: Yui Ota, Tokyo (JP); Ikuo Goto, Tokyo (JP)

(73) Assignee: SUBARU CORPORATION, Tokyo (JP)

(*) Notice: Subject to any disclaimer, the term of this patent is extended or adjusted under 35 U.S.C. 154(b) by 458 days.

(21) Appl. No.: 17/138,887

(22) Filed: Dec. 30, 2020

(65) Prior Publication Data

US 2021/0261164 A1 Aug. 26, 2021

(30) Foreign Application Priority Data

Feb. 21, 2020 (JP) ................. 2020-027868

(51) Int. Cl.
 *B60W 60/00* (2020.01)
 *G08G 1/16* (2006.01)
 (Continued)

(52) U.S. Cl.
 CPC ..... *B60W 60/0051* (2020.02); *A61B 5/02055* (2013.01); *A61B 5/1077* (2013.01);
 (Continued)

(58) Field of Classification Search
 CPC ............ B60W 60/0051; B60W 40/08; B60W 2040/0818; B60W 2540/22; B60W 2540/221; A61B 5/02055; A61B 5/1077; A61B 5/14532; A61B 5/369; A61B 5/747; A61B 5/021; A61B 5/024; A61B 5/18; A61B 5/6893; G08G 1/087; G08G 1/162; G08G 1/096811; G08G 1/09685; G08G 1/07; G06V 20/597; G06V 20/56; G01C 21/34

See application file for complete search history.

(56) References Cited

U.S. PATENT DOCUMENTS

2018/0315298 A1* 11/2018 Kitamura ............. G08B 25/014

FOREIGN PATENT DOCUMENTS

JP 2017-177932 A 10/2017
JP 2018-190142 A 11/2018

* cited by examiner

*Primary Examiner* — Yuen Wong
(74) *Attorney, Agent, or Firm* — McDermott Will & Emery LLP

(57) ABSTRACT

A vehicle controller includes a processor that switches, when detecting a physical abnormality of an occupant of an own vehicle based on physical information of the occupant, the own vehicle to an emergency mode in which the own vehicle automatically travels to a destination. The processor receives, when the own vehicle is switched to the emergency mode, other vehicle information from another vehicle switched to the emergency mode. The other vehicle information includes information on a physical abnormality of an occupant of the other vehicle. Based on the other vehicle information and own vehicle information including information on the physical abnormality of the occupant of the own vehicle, the processor sets the order of priority to determine which of the own vehicle or the other vehicle is allowed to travel preferentially, and sends, based on the order of priority, a medical aid request to an information processor.

17 Claims, 7 Drawing Sheets

(51) Int. Cl.
*G08G 1/087* (2006.01)
*A61B 5/107* (2006.01)
*A61B 5/0205* (2006.01)
*A61B 5/145* (2006.01)
*A61B 5/00* (2006.01)
*B60W 40/08* (2012.01)
*A61B 5/369* (2021.01)
*A61B 5/024* (2006.01)
*A61B 5/021* (2006.01)
*G06V 20/59* (2022.01)

(52) U.S. Cl.
CPC .......... *A61B 5/14532* (2013.01); *A61B 5/369* (2021.01); *A61B 5/747* (2013.01); *B60W 40/08* (2013.01); *G08G 1/087* (2013.01); *G08G 1/162* (2013.01); *A61B 5/021* (2013.01); *A61B 5/024* (2013.01); *B60W 2040/0818* (2013.01); *G06V 20/597* (2022.01)

VEHICLE CONTROLLER AND VEHICLE CONTROL SYSTEM

CROSS-REFERENCE TO RELATED APPLICATIONS

The present application claims priority from Japanese Patent Application No. 2020-027868 filed on Feb. 21, 2020, the entire contents of which are hereby incorporated by reference.

BACKGROUND

The technology relates to a vehicle controller and a vehicle control system.

A system has been proposed for rescuing a driver in an emergency state of being unable to drive a vehicle. Reference is made to Japanese Unexamined Patent Application Publication (JP-A) Nos. 2017-177932 and 2018-190142.

SUMMARY

An aspect of the technology provides a vehicle controller including a processor. The processor is configured to switch, when detecting a physical abnormality of an occupant of an own vehicle on the basis of physical information of the occupant of the own vehicle, the own vehicle to an emergency mode in which the own vehicle is caused to automatically travel to a predetermined destination. The processor is configured to receive, in a case where the own vehicle is switched to the emergency mode, other vehicle information from another vehicle switched to the emergency mode together with the own vehicle. The other vehicle information includes at least information on a physical abnormality of an occupant of the other vehicle. The processor is configured to set, on the basis of the other vehicle information received and own vehicle information including information on the physical abnormality of the occupant of the own vehicle, an order of priority between the own vehicle and the other vehicle to determine which of the own vehicle or the other vehicle is allowed to travel preferentially, and send a medical aid request to an information processor on the basis of the order of priority set. The information processor is configured to output control data to the other vehicle and a traffic light.

An aspect of the technology provides a vehicle control system including: a vehicle-side controller configured to control an own vehicle; and an information processor configured to transmit control data to the own vehicle, another vehicle, and a traffic light management device. The vehicle-side controller includes an emergency mode setting section and a transmitter. The emergency mode setting section is configured to switch, when detecting a physical abnormality of an occupant of the own vehicle on the basis of physical information of the occupant of the own vehicle, the own vehicle to an emergency mode in which the own vehicle is caused to automatically travel to a predetermined destination. The transmitter is configured to send a medical aid request to the information processor in a case where the own vehicle is switched to the emergency mode. The medical aid request includes information on the physical abnormality of the occupant of the own vehicle and requests to control the other vehicle and a traffic light to allow the own vehicle to travel preferentially. The information processor includes a control data generating unit and a control data transmitter. The control data generating unit is configured to generate control data for the own vehicle, the other vehicle, and the traffic light management device on the basis of the medical aid request. The control data transmitter is configured to transmit the control data for the own vehicle, the other vehicle, and the traffic light management device to the own vehicle, the other vehicle, and the traffic light management device. In a case where the other vehicle is switched to the emergency mode together with the own vehicle, the control data generating unit is configured to generate the control data for the own vehicle, the other vehicle, and the traffic light management device on the basis of the information on the physical abnormality of the occupant of the own vehicle switched to the emergency mode and information on a physical abnormality of an occupant of the other vehicle switched to the emergency mode, to allow either one of the own vehicle and the other vehicle to travel preferentially.

An aspect of the technology provides a vehicle control system including: a vehicle-side controller configured to control an own vehicle; and an information processor configured to transmit control data to the own vehicle, another vehicle, and a traffic light management device. The vehicle-side controller includes circuitry configured to: switch, when detecting a physical abnormality of an occupant of the own vehicle on the basis of physical information of the occupant of the own vehicle, the own vehicle to an emergency mode in which the own vehicle is caused to automatically travel to a predetermined destination; and send a medical aid request to the information processor in a case where the own vehicle is switched to the emergency mode. The medical aid request includes information on the physical abnormality of the occupant of the own vehicle and requesting the information processor to control the other vehicle and a traffic light to allow the own vehicle to travel preferentially. The information processor includes circuitry configured to: generate control data for the own vehicle, the other vehicle, and the traffic light management device on the basis of the medical aid request; and transmit the control data for the own vehicle, the other vehicle, and the traffic light management device to the own vehicle, the other vehicle, and the traffic light management device. In a case where the other vehicle is switched to the emergency mode together with the own vehicle, the circuitry is configured to generate the control data for the own vehicle, the other vehicle, and the traffic light management device on the basis of the information on the physical abnormality of the occupant of the own vehicle switched to the emergency mode and information on a physical abnormality of an occupant of the other vehicle switched to the emergency mode, to allow either one of the own vehicle and the other vehicle to travel preferentially.

BRIEF DESCRIPTION OF THE DRAWINGS

The accompanying drawings are included to provide a further understanding of the technology and are incorporated in and constitute a part of this specification. The drawings illustrate example embodiments and, together with the specification, serve to explain the principles of the technology.

DETAILED DESCRIPTION

Figure 1:
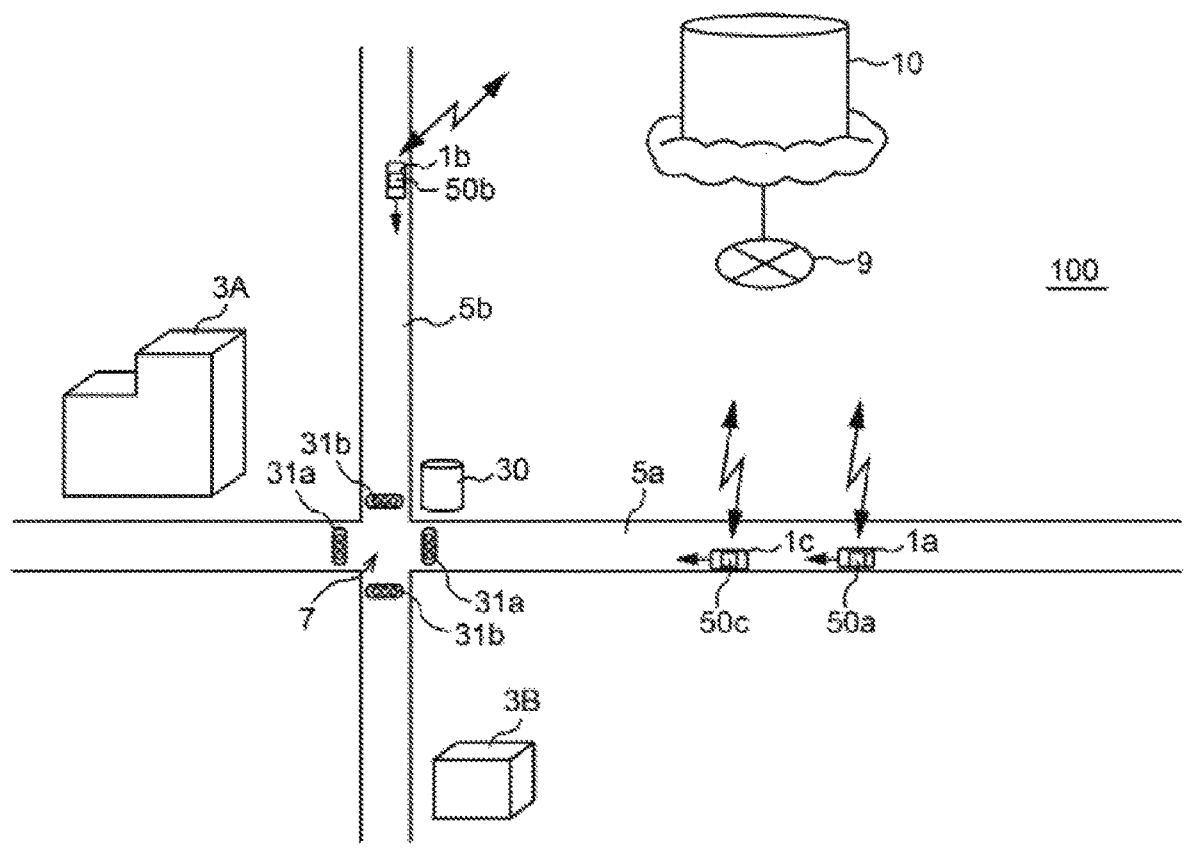
FIG. 1 is a schematic diagram illustrating a vehicle control system according to one example embodiment of the technology.

JP-A No. 2017-177932 discloses an emergency response system including a vehicle-side apparatus and a center-side apparatus. The vehicle-side apparatus includes: a drive determination unit that determines whether a driver is able to drive the vehicle on the basis of the state of the driver; a stop transmitter that stops the vehicle when the drive determination unit determines that the driver is unable to drive the vehicle and transmits biological information of the driver and vehicle information to the center-side apparatus; and an automated driving unit that automatically drives the vehicle to a destination. The center-side apparatus includes an arrangement unit that calls for an ambulance or transmits data on the location of a medical institution and data instructing automated driving of the vehicle to the vehicle-side apparatus on the basis of the biological information of the driver and the vehicle information. When receiving the data instructing automated driving of the vehicle, the vehicle-side apparatus designates the location of the medical institution as the destination and executes the automated driving to the destination.

JP-A No. 2018-190142 discloses an emergency transport arrangement apparatus that addresses a shortage of emergency vehicles. According to JP-A No. 2018-190142, the emergency transport arrangement apparatus selects an emergency vehicle present near a patient (not an occupant in a vehicle in a vehicle in JP-A No. 2018-190142) in an emergency state from a plurality of emergency vehicles to be used for transporting patients to medical institutions, instruct the selected emergency vehicle to automatically travel to the patient to pick up the patient, and transports the patient to a medical institution. To transport the patient to the medical institution, the emergency transport arrangement apparatus calculates a route to the patient and a route to the medical institution on the basis of data on position of the patient, data on location of the emergency vehicles, and data on location of the medical institution. On the basis of the calculated routes, the emergency transport arrangement apparatus switches traffic lights of a traffic system so as to shorten the time waiting for a traffic signal to change.

JP-A Nos. 2017-177932 and 2018-190142 fail to consider that there can be a case where a plurality of emergency vehicles are traveling in the same area at the same time. For example, JP-A No. 2017-177932 fails to disclose a measure against the case where a plurality of vehicles each accommodating an occupant in an emergency state of being unable to drive the vehicle enter an intersection at the same time on the way to respective medical institutions. JP-A No. 2018-190142 fails to disclose a measure to switch traffic lights when a plurality of emergency vehicles enter an intersection at the same time. The degree of urgency of physical abnormality of the occupant can differ depending on a physical condition or a symptom of the occupant. Thus, it is desired to allow a vehicle accommodating an occupant of a high degree of urgency to travel preferentially over the other vehicles each accommodating an occupant of a low degree of urgency.

It is desirable to provide a vehicle controller and a vehicle control system that set an order of priority between a plurality of vehicles defined as emergency vehicles and causes each of the emergency vehicles to an appropriate destination.

Some embodiments of the technology will now be described in detail with reference to the accompanying drawings. Note that the following description is directed to illustrative examples of the technology and not to be construed as limiting to the technology. Factors including, without limitation, numerical values, shapes, materials, components, positions of the components, and how the components are coupled to each other are illustrative only and not to be construed as limiting to the technology. Further, elements in the following example embodiments that are not recited in a most-generic independent claim of the technology are optional and may be provided on an as-needed basis. The drawings are schematic and are not intended to be drawn to scale. Throughout the present specification and the drawings, elements having substantially the same function and configuration are denoted with the same numerals to avoid any redundant description.

First Example Embodiment

[1. Example Configuration of Vehicle Control System]

Figure 2:
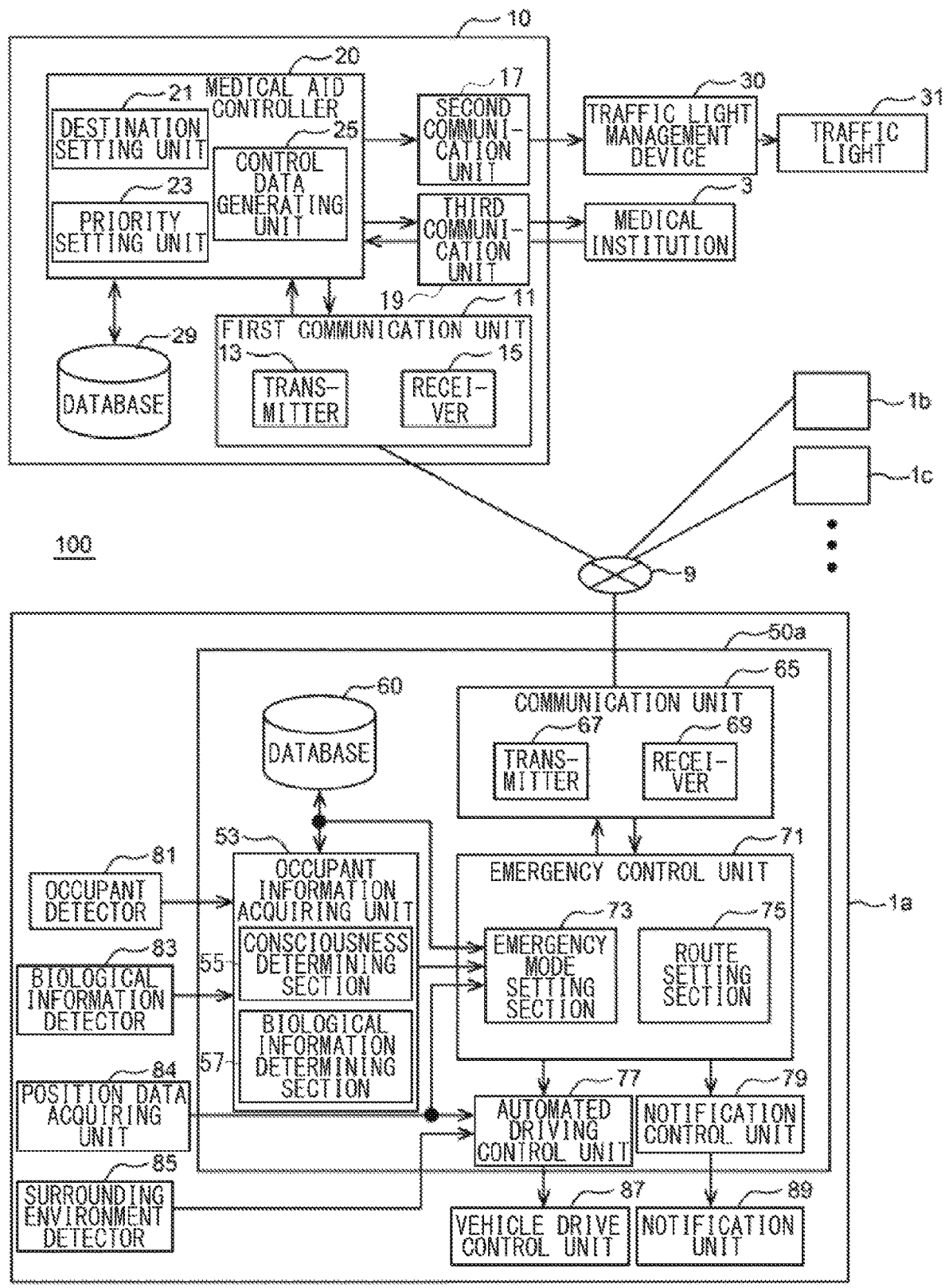
FIG. 2 is a block diagram illustrating an example configuration of the vehicle control system.

Now described is an example configuration of a vehicle control system according to an example embodiment of the technology. FIG. 1 schematically illustrates a vehicle control system 100 according to a first example embodiment of the technology. FIG. 2 is a block diagram of an example configuration of the vehicle control system 100 according to the first example embodiment of the technology.

With reference to FIG. 1, the vehicle control system 100 includes vehicle-side controllers 50a to 50c provided in respective vehicles 1a to 1c, and an information processor 10 configured to communicate with the vehicle-side controllers 50a to 50c. The information processor 10 may also be configured to communicate with a traffic light management device 30 and medical institutions 3A and 3B. When any of the vehicles 1a to 1c is switched to an emergency mode, the vehicle control system 100 may output control data to the other vehicles and the traffic light management device 30 to control traffic lights 31a to 31b so that the vehicle switched to the emergency mode (hereinafter also referred to as an emergency vehicle) is caused to automatically travel to a destination smoothly.

In a case where a plurality of vehicles (e.g., the vehicles 1a and 1b) are defined as the emergency vehicles at the same time, the vehicle control system 100 may set an order of priority between the vehicles 1a and 1b. In a case where the vehicle 1a has a high priority, for example, the vehicle control system 100 may control the other vehicles 1b and 1c and the traffic lights 31a to 31b so that the vehicle 1a is allowed to travel preferentially over the other vehicles 1b and 1c.

In the case of the vehicle 1a being defined as an emergency vehicle of high priority, the vehicle 1b being defined as an emergency vehicle of low priority, and the vehicle 1c being defined as an ordinary vehicle not being switched to the emergency mode, the vehicle 1c defined as the ordinary vehicle may be controlled or notified so as not to hinder overtaking of the vehicle 1a defined as the emergency vehicle of high priority, and the vehicle 1b defined as the emergency vehicle of low priority may be controlled or notified so as not to enter an intersection 7. In a case where the vehicles 1a and 1b defined as the emergency vehicles reach the intersection 7 at the same time, the traffic light 31a on a road 5a on which the vehicle 1a defined as the emergency vehicle of high priority is traveling may be switched to green, and the traffic light 31b on a road 5b on which the vehicle 1b defined as the emergency vehicle of low priority is traveling may be switched to red. This allows the vehicle 1a defined as the emergency vehicle of high priority to travel preferentially over the other vehicles, while guiding all the emergency vehicles (i.e., the vehicles 1a and 1b) to the respective medical institutions 3A and 3B smoothly.

Hereinafter, the vehicle-side controllers 50a to 50c may also be referred to as vehicle-side controllers 50, the medical institutions 3A and 3B as medical institutions 3, the traffic lights 31a to 31b as traffic lights 31, and the roads 5a and 5b as roads 5 when there is no need to distinguish them.

Now, with reference to FIG. 2, the example configuration of the vehicle control system 100 is described in detail. The description of the example configuration of the vehicle control system 100 may be divided into the description of the vehicle-side controller 50a and the description of the information processor 10. Although only the vehicle-side controller 50a mounted in the vehicle 1a is illustrated in FIG. 2, the vehicle-side controllers 50b and 50c mounted in the respective vehicles 1b and 1c may have the same configuration as the vehicle-side controller 50a.

[1-1. Vehicle-Side Controller]

The vehicle-side controller 50a may be mounted in the vehicle 1a. The vehicle-side controller 50a acquires biological information of the occupant. When detecting a physical abnormality of the occupant on the basis of the biological information, the vehicle-side controller 50a switches a control mode of the vehicle 1a to an emergency mode, and sends a medical aid request including information on the physical abnormality to the information processor 10. Further, the vehicle-side controller 50a may acquire information on the driving state of the vehicle 1a and information on surrounding environment of the vehicle 1a. On the basis of the information acquired, the vehicle-side controller 50a may perform automated driving control of the vehicle 1a to cause the vehicle 1a to travel to the medical institution 3A designated as a destination.

The vehicle-side controller 50a may include an arithmetic processing unit, such as a central processing unit (CPU) or a micro-processing unit (MPU), and a memory, such as a random access memory (RAM) or a read only memory (ROM), for example. The arithmetic processing unit may execute programs stored in the memory to conduct various calculation processes. In addition to or in place of the memory, the vehicle-side controller 50a may include a storage medium, such as a hard disk drive (HDD), a compact disc (CD), a digital versatile disc (DVD), a solid state drive (SSD), a universal serial bus (USB) flash drive, or another storage device. Note that a portion or the entirety of the vehicle-side controller 50a may be updatable software such as firmware, or a program module to be executed in response to a command from the CPU, for example.

For example, the vehicle-side controller 50a may include a communication unit 65, a database 60, an occupant information acquiring unit 53, emergency control unit 71, an automated driving control unit 77, and a notification control unit 79. Out of these components, the occupant information acquiring unit 53, the emergency control unit 71, the automated driving control unit 77, and the notification control unit 79 may be implemented by programs executed by the arithmetic processing unit. Further, an occupant detector 81, a biological information detector 83, a position data acquiring unit 84, a surrounding environment detector 85, a vehicle drive control unit 87, and a notification unit 89 may be coupled to the vehicle-side controller 50a.

[1-1-1. Occupant Detector]

The occupant detector 81 may be provided inside the vehicle and detect an occupant, such as a driver or a passenger, in the vehicle 1a. The occupant information acquiring unit 53 may receive information on the detection by the occupant detector 81. In the example embodiment, the occupant detector 81 may include a camera that captures an image of the interior of the vehicle compartment, and an image processor that specifies an individual occupant on the basis of the image data acquired by the camera. The image processor may specify the facial orientation, facial expression, and facial movement of the occupant detected by processing the image data. Alternatively, the occupant detector 81 may calculate the facial feature quantity of the detected occupant to select a person corresponding to the detected occupant from persons registered in advance.

[1-1-2. Biological Information Detector]

The biological information detector 83 may include one or more detectors that acquire biological information of the occupant. The occupant information acquiring unit 53 may receive the biological information acquired by the biological information detector 83. Alternatively, the camera and the image processor of the occupant detector 81 may serve as the biological information detector 83. In such a case, the image processor may acquire the biological information, such as the heart rate, pulse rate, or temperature of the occupant on the basis of a change in color of the facial image captured by the camera, for example. The biological information detector 83 may further include one or more of the following devices including, for example, a Doppler sensor that detects the heart rate of the occupant using an electromagnetic wave, a non-contact pulse sensor that detects the pulse rate of the occupant, an electrode embedded in the steering wheel to measure the heart rate or the electrocardiogram of the driver, a pressure instrument embedded in the driver's seat to measure the sitting pressure distribution while the occupant is seated on the seat, a device that detects a change in the position of the seatbelt to measure the heart rate or the breathing rate of the occupant, a time of flight (TOF) sensor that acquires information on position (biological position) of the occupant, and a thermographic device measuring the skin surface temperature of the occupant. The biological information detector 83 may further include a mountable detector, such as a wearable device, that acquires the biological information of the occupant while being mounted on the occupant.

[1-1-3. Position Information Acquiring Unit]

The position data acquiring unit 84 may acquire information on traveling position of the vehicle 1a on map data. The position data acquiring unit 84 should not be limited to a particular unit and may be any unit that acquires the information on traveling position of the vehicle 1a. For example, the position data acquiring unit 84 may be a global positioning system (GPS) antenna that receives satellite signals from the GPS satellites. The emergency control unit 71 and the automated driving control unit 77 may receive the position information acquired by the position data acquiring unit 84.

[1-1-4. Surrounding Environment Detector]

The surrounding environment detector 85 may acquire information on surrounding environment of the vehicle 1a. The automated driving control unit 77 may receive the information acquired by the surrounding environment detector 85. The surrounding environment detector 85 may detect persons, other vehicles, bicycles, buildings, and other obstacles present around the vehicle 1a to acquire the information on surrounding environment of the vehicle 1a. For example, the surrounding environment detector 85 may include one or more of the following devices including, for example, a camera that captures an image of the surrounding environment of the vehicle 1a, a radar that detects an object present around the vehicle 1a, and a detector, such as a LiDAR, that detects the distance or azimuth to the object present around the vehicle 1a. The surrounding environment detector 85 may further include a communication device that acquires information from a device outside the vehicle 1a via a vehicle-to-vehicle communication or a road-to-vehicle communication, for example.

[1-1-5. Vehicle Drive Control Unit]

The vehicle drive control unit 87 may include one or more control sections that cause the vehicle 1a to travel. For example, the vehicle drive control unit 87 may include a control section that controls driving of an engine, a power transmission mechanism including one or more drive motors and a transmission, a steering system, and a brake system. In this example embodiment, the vehicle drive control unit 87 may control devices to be controlled on the basis of control data received from the automated driving control unit 77. The vehicle drive control unit 87 may automatically control a part or the entirety of the travel of the vehicle regardless of driver's operations, causing the vehicle to travel to a destination along a predetermined traveling route.

[1-1-6. Notification Unit]

The notification unit 89 may notify the occupant of the vehicle 1a of predetermined information. The notification unit 89 may be a display or a speaker, for example. The notification unit 89 may make predetermined notification on the basis of control data received from the notification control unit 79. In this example embodiment, the notification unit 89 may notify the occupant of at least a setting status of the emergency mode, information on the destination, and information on a transport route to the destination. The notification unit 89 may include a notification section that notifies a person outside the vehicle 1a of at least the emergency mode being set.

[1-1-7. Communicating Unit]

The communication unit 65 may be an interface used to exchange information between the vehicle-side controller 50 and the information processor 10. The communication unit 65 may include a transmitter 67 and a receiver 69. In this example embodiment, the communication unit 65 may be a communication interface accessible to the information processor 10 via a mobile communication network 9.

[1-1-8. Database]

The database 60 may be a storage medium that stores information on the attribution of the occupant, and the biological information of the occupant measured in a normal traveling of the vehicle without the emergency mode being set. The database 60 may include facial image data or facial feature quantity data to be used to identify the occupant on the basis of the facial image acquired by the occupant detector 81. The database 60 may include, as the information on the attribution of the occupant, pre-registered information on chronic diseases or the medical history of the occupant. The occupant information acquiring unit 53 and the emergency control unit 71 may be accessible to the information stored in the database 60.

[1-1-9. Occupant Information Acquiring Unit]

The occupant information acquiring unit 53 may acquire information on the occupant on the basis of the information acquired by the occupant detector 81, the information acquired by the biological information detector 83, and the information stored in the database 60. The occupant information acquiring unit 53 may include a consciousness determining section 55 and a biological information determining section 57. The consciousness determining section 55 may determine whether the occupant is unconscious on the basis of the information received from the occupant detector 81. For example, in a case where the occupant has been motionless with his/her head bent down or with his/her eyes downcast for a predetermined time or longer, the consciousness determining section 55 may determine that the occupant is unconscious. Alternatively, in a case where the occupant has been motionless with his/her eyes closed for a predetermined time or longer, the consciousness determining section 55 may determine that the occupant is unconscious. In a case where the consciousness determining section 55 finds it difficult to determine whether the occupant is sleeping or unconscious, the consciousness determining section 55 may apply a stimulus, such as a sound, a voice, or a vibration, at a predetermined intensity to the occupant for a predetermined time or longer. If the occupant does not respond to the stimulus, the consciousness determining section 55 may determine that the occupant is unconscious.

The biological information determining section 57 may acquire the biological information of the occupant on the basis of the information received from the occupant detector 81 and/or the information received the biological information detector 83. For example, the biological information determining section 57 may detect one or more of the heart rate, pulse rate, temperature, blood pressure, breathing rate, blood glucose level, and brain waves of the occupant. For example, the biological information determining section 57 may estimate the biological information, such as the heart rate, pulse rate, temperature, and blood pressure, of the occupant on the basis of a change in color of the facial image acquired by the occupant detector 81. Further, the biological information determining section 57 may estimate the pulse rate or the heart rate of the occupant on the basis of a sensor output from the pulse rate sensor or the Doppler sensor using an electromagnetic wave. Further, the biological information determining section 57 may estimate the heart rate or the electrocardiogram of the driver on the basis of an output voltage from the electrode embedded in the steering wheel. Further, the biological information determining section 57 may estimate the heart rate or the breathing rate of the occupant on the basis of an output from the device detecting a change in position of the seatbelt. Further, the biological information determining section 57 may estimate the skin surface temperature of the occupant on the basis of an output from the thermographic device.

The biological information determining section 57 may correlate the estimated biological data with the attribution of the occupant and accumulate the resultant data in the database 60. The biological information determining section 57 may accumulate the biological data together with the information on the setting status of the emergency mode in the database 60. The biological information stored in the database 60 may be the biological information measured in the normal traveling of the vehicle without the emergency mode being set, as described above. The biological information stored in the database 60 may be regarded as a normal range of the biological information of an individual occupant. The occupant information acquiring unit 53 may output, to the emergency control unit 71, information on the results of determination by the consciousness determining section 55 and information on the results of determination by the biological information determining section 57 as physical information of the occupant.

[1-1-10. Emergency Controller]

The emergency control unit 71 may determine the occurrence or absence of physical abnormality of the occupant. When detecting the occurrence of physical abnormality of the occupant, the emergency control unit 71 may switch the control mode of the vehicle 1a to the emergency mode to define the vehicle 1a as an emergency vehicle. The emergency control unit 71 may include an emergency mode setting section 73 and a route setting section 75. When detecting the occurrence of physical abnormality of the occupant on the basis of the physical information of the occupant received from the occupant information acquiring unit 53, the emergency mode setting section 73 may switch the control mode of the vehicle 1a to the emergency mode in which the vehicle 1a is caused to automatically travel to a predetermined destination. In the example embodiment, the emergency control unit 71 may determine the occurrence or absence of physical abnormality of the occupant on the basis of the information on the results of determination by the consciousness determining section 55 and the information on the results of determination by the biological information determining section 57.

For example, in a case where the estimated biological information differs largely from the normal range of the biological information of the occupant and where the occupant is unconscious, the emergency mode setting section 73 may determine the occurrence of physical abnormality of a high degree of urgency in the occupant. In such a case, the emergency mode setting section 73 may switch the control mode of the vehicle 1a to the emergency mode. In a case where the estimated biological information differs moderately from the normal range of the biological information of the occupant, the emergency mode setting section 73 may determine the occurrence of physical abnormality of a moderate degree of urgency in the occupant. In such a case, the emergency mode setting section 73 may switch the control mode of the vehicle 1a to the emergency mode. In a case where the estimated biological information differs slightly from the normal range of the biological information of the occupant, the emergency mode setting section 73 may determine the occurrence of physical abnormality of a low degree of urgency in the occupant. In such a case, the emergency mode setting section 73 may switch the control mode of the vehicle 1a to the emergency mode. In contrast, in a case where the estimated biological information falls within the normal range of the biological information of the occupant and where the occupant is conscious, the emergency mode setting section 73 may determine the absence of physical abnormality in the occupant. In such a case, the emergency mode setting section 73 may not switch the control mode of the vehicle 1a to the emergency mode.

When detecting the occurrence of physical abnormality of the occupant on the basis of the determination as to whether the occupant is unconscious and the results of estimation of the biological information, the emergency mode setting section 73 may perform a sound output process that causes a speaker to output a sound or voice asking if the occupant finds himself or herself having a physical abnormality. On the basis of the presence or absence of a response or the content of the response acquired via a microphone, the emergency mode setting section 73 may determine the occurrence or absence of physical abnormality of the occupant.

Upon switching of the control mode of the vehicle 1a to the emergency mode, the emergency mode setting section 73 may send a medical aid request to the information processor via the transmitter 67. The medical aid request may include the information on the physical abnormality of the occupant, and request the information processor to control the other vehicles and the traffic lights 31 so that the own vehicle (i.e., the vehicle 1a) is allowed to travel preferentially over the other vehicles. The information on the physical abnormality of the occupant may include the estimated biological information and the information on the degree of urgency. Optionally, the information on the physical abnormality of the occupant may include the information on chronic diseases or the medical history of the occupant retrieved from the database 60. The medical aid request may also include the information on current position of the own vehicle (i.e., the vehicle 1a). The information transmitted to the information processor 10 may be used to designate any of the medical institutions 3 as a destination, and set a transport route to the medical institution 3 and the order of priority among a plurality of emergency vehicles, if any.

On the basis of the information on the medical institution 3 designated as the destination and the information on the transport route to the medical institution 3 received from the information processor 10 via the receiver 69, the route setting section 75 may set a destination of the vehicle 1a traveling under the automated driving control, and a traveling route to the destination.

[1-1-11. Automated Driving Control Unit]

The automated driving control unit 77 may perform the automated driving control of the vehicle 1a. For example, the automated driving control unit 77 may generate a control signal to be sent to the vehicle drive control unit 87 on the basis of the information on current position of the vehicle 1a received from the position data acquiring unit 84, the information on surrounding environment of the vehicle 1a received from the surrounding environment detector 85, and information on the destination and the traveling route set by the route setting section 75. For example, the automated driving control unit 77 may generate information on target values of the steering angle, vehicle speed, acceleration rate, and braking force of the vehicle 1a to cause the vehicle 1a to travel avoiding a contact with other vehicles, persons, or obstacles present around the vehicle 1a along the traveling route to the destination. The automated driving control unit 77 may send the generated information to the vehicle drive control unit 87.

[1-1-12. Notification Control Unit]

The notification control unit 79 may generate a control signal to be sent to the notification unit 89. In response to the control signal, the notification unit 89 may make predetermined notification. The notification control unit 79 may cause the notification unit 89 to make notification of at least of switching of the control mode of the vehicle 1a to the emergency mode or the medical institution 3A being designated as the destination. In addition to such notification, the notification control unit 79 may cause the notification unit 89 to make notification of at least one of a scheduled arrival time to the medical institution 3A, a traveling route to the medical institution 3A, or the order of priority of the vehicle 1a.

[1.2. Information Processor]

When receiving the medical aid request from the vehicle-side controllers 50a and 50b of the respective vehicles 1a and 1b defined as the emergency vehicles, the information processor 10 generates control data for the vehicles 1a, 1b, and 1c and the traffic light management device 30 on the basis of the medical aid request. On the basis of the control data, the vehicles 1a and 1b are allowed to travel preferentially over the other vehicles. For example, the other vehicle 1c traveling on the same road or traveling through the same intersection as the vehicles 1a and 1b defined as the emergency vehicles may be decelerated or stopped so that the vehicles 1a and 1b defined as the emergency vehicles are allowed to travel preferentially over the other vehicle 1c. Additionally, the traffic lights 31 may be controlled so that the traffic lights 31 in front of the emergency vehicles (i.e., the vehicles 1a and 1b) traveling in respective advancing directions are switched to green. In such a case where a plurality of vehicles (e.g., the vehicles 1a and 1b) are defined as the emergency vehicles, the information processor 10 may generate control data for the vehicles 1a to 1c and the traffic light management device 30. On the basis of the control data, the vehicle 1a or 1b may be allowed to travel preferentially over the other vehicles on the basis of the information on physical abnormality of the occupant included in the medical aid request.

Further, the information processor 10 according to the example embodiment may designate the medical institutions 3A and 3B as the destinations of the respective vehicles 1a and 1b defined as the emergency vehicles switched to the emergency mode. This allows the vehicles 1a and 1b to travel to appropriate destinations even if the users or drivers of the vehicles 1a and 1b are unable to set a destination because of being unconscious, for example.

The information processor 10 may include an arithmetic processing unit such as CPU and a storage medium as appropriate. The information processor 10 may be configured to communicate with the vehicle-side controller 50 via at least the mobile communication network 9. A representative example of the information processor 10 may be a cloud server; however, the information processor 10 may be another server.

The information processor 10 may include a first communication unit 11, a second communication unit 17, a third communication unit 19, a database 29, and a medical aid controller 20. Among these units, the medical aid controller 20 may be implemented by a program executed by the arithmetic processing unit.

[1-2-1. First Communication Unit]

The first communication unit 11 may be an interface used to exchange information between the information processor 10 and the vehicle-side controller 50 mounted in each of the vehicles 1. The first communication unit 11 may include a transmitter 13 and a receiver 15. The transmitter 13 may serve as a part of a control data transmitter that transmits the control data generated on the basis of the medical aid request. In this example embodiment, the first communication unit 11 may be a communication interface accessible to the vehicle-side controller 50 via the mobile communication network 9.

[1-2-2. Second Communication Unit]

The second communication unit 17 may be an interface used to transmit the control data from the information processor 10 to the traffic light management device 30. The second communication unit 17 may serve as a part of the control data transmitter that transmits the control data generated on the basis of the medical aid request. The second communication unit 17 may transmit the control data to the traffic light management device 30 via a dedicated line or a communication network such as the Internet. The traffic light management device 30 may control switching of the indication of the traffic lights 31 installed at an intersection, for example. The traffic light management device 30 may switch the traffic lights 31 on the basis of the received control data while the vehicles 1a and 1b defined as the emergency vehicles are traveling.

[1-2-3. Third Communication Unit]

The third communication unit 19 may be an interface used to exchange information between the information processor 10 and each of the medical institutions 3. The third communication unit 19 may serve as a part of the control data transmitter that transmits the control data generated on the basis of the medical aid request. The third communication unit 19 may be accessible to each of the medical institutions 3 via a dedicated line or a communication network such as the Internet. Each of the medical institutions 3 may send a reply of acceptance or rejection in response to an inquiry about acceptance sent from the information processor 10

[1-2-4. Database]

The database 29 may be a storage medium that stores data on the medical institutions 3. The data on the medical institutions 3 may include pre-registered information on the address, clinical departments, number of beds, and availability of emergency medical services of each medical institution 3.

[1-2-5. Medical Aid Controller]

The medical aid controller 20 may set destinations of the vehicles 1a and 1b defined as the emergency vehicles on the basis of the medical aid request received from the vehicles 1a and 1b defined as the emergency vehicles, set the order of priority between the vehicles 1a and 1b defined as the emergency vehicles, and generate control data to cause the vehicles 1a and 1b defined as the emergency vehicles to travel to the respective medical institutions 3 designated as the destinations to which the vehicles 1a and 1b defined as the emergency vehicles are to be transported. The medical aid controller 20 may include a destination setting unit 21, a priority setting unit 23, and a control data generating unit 25.

Referring to the database 29, the destination setting unit 21 may select, from the medical institutions 3, potential destinations to which the vehicles 1a and 1b defined as the emergency vehicles are to be transported on the basis of the medical aid requests received from the vehicles 1a and 1b defined as the emergency vehicles. For example, the destination setting unit 21 may select, as potential destinations of the vehicles 1a and 1b, the medical institutions 3 located within a predetermined range from the current positions of the vehicles 1a and 1b defined as the emergency vehicles and able to offer a medical service to the occupants on the basis of the information on current positions of the vehicles 1a and 1b defined as the emergency vehicles and the information on chronic diseases and medical history of the occupant used to estimate a physical abnormality of the occupant. The destination setting unit 21 may send the inquiry about acceptance to the selected medical institutions 3 via the third communication unit 19. In addition to the inquiry about acceptance, the destination setting unit 21 may transmit the information on the physical abnormality of the occupant, the degree of urgency, and the current position of the vehicles 1a or 1b.

When receiving a reply of rejection from the medical institution 3 to which the inquiry about acceptance has been sent, the destination setting unit 21 may select another medical institution 3 and send the inquiry about acceptance to the selected medical institution 3. The destination setting unit 21 may repeat selecting a potential medical institution 3 and sending the inquiry about acceptance until receiving a reply of acceptance from any of the medical institutions 3. When receiving a reply of acceptance from each of the selected medical institutions 3, the destination setting unit 21 may designate the medical institutions 3 as the destinations to which the vehicle 1a and 1b defined as the emergency vehicles are to be transported.

When receiving the medical aid requests from the vehicles 1a and 1b defined as the emergency vehicles, the priority setting unit 23 may set the order of priority between the vehicles 1a and 1b defined as the emergency vehicles. In other words, the priority setting unit 23 may determine which vehicle 1a or 1b is to be allowed to travel preferentially. As described above, the medical aid request sent from each of the vehicles 1a and 1b defined as the emergency vehicles may include the information on the degree of urgency of physical abnormality of the occupant. The priority setting unit 23 may set a higher priority to the vehicle 1a or 1b, whichever is of higher degree of urgency. In a case where the same degree of urgency is set to a plurality of vehicles, the priority setting unit 23 may set the order of priority on the basis of the chronic diseases or the medical history of the occupant included in the medical aid request. The order of priority based on the chronic diseases and the medical history may be stored in the database 29 in advance.

The control data generating unit 25 may generate control data for the vehicles 1a and 1b defined as the emergency vehicles, the vehicle 1c defined as the ordinary vehicle, and the traffic light management device 30 on the basis of: the information on the medical institutions 3 designated as the destinations by the destination setting unit 21; the information on the transport routes to the medical institutions 3; the order of priority set by the priority setting unit 23 between the vehicles 1a and 1b defined as the emergency vehicles; and the medical aid requests sent from the vehicle-side controllers 50. The control data generating unit 25 may transmit the generated control data to the respective vehicles 1 and the traffic light management device 30 via the first communication unit 11 and the second communication unit 17.

For example, the control data generating unit 25 may transmit the information on the medical institution 3 designated as the destination and the information on the transport route to the medical institution 3 to each of the vehicles 1a and 1b defined as the emergency vehicles. When receiving the information on the medical institution 3 and the information on the transport route to the medical institution 3, the vehicle-side controller 50 of each of the vehicles 1a and 1b defined as the emergency vehicles may designate the medical institution 3 as the destination and set the transport route to the medical institution 3 as a traveling route, and perform the automated driving control. The control data generating unit 25 may sequentially receive the information on current positions of the vehicles 1 from the vehicles 1, generate control data to cause the traffic lights 31 in front of the vehicle 1a and 1b defined as the emergency vehicles and traveling in respective advancing directions to switch to green, and transmit the control data to the traffic light management device 30.

Further, the control data generating unit 25 may sequentially receive the information on current positions of the vehicles 1 from the vehicles 1, generate control data to cause the vehicle 1c defined as the ordinary vehicle to travel so as not hinder the travel of the vehicles 1a and 1b defined as the emergency vehicles, and send the control data to the vehicle 1c defined as the ordinary vehicle. In a case where the vehicle 1c defined as the ordinary vehicle is traveling under the automated driving control, the control data generating unit 25 may generate a control signal to decelerate or stop the vehicle 1c defined as the ordinary vehicle, a control signal to set a traveling path of the vehicle 1c defined as the ordinary vehicle so that the vehicles 1a and 1b defined as the emergency vehicles readily overtake the vehicle 1c, or a control signal to change the traveling route of the vehicle 1c defined as the ordinary vehicle. The control data generating unit 25 may then send the control signal to the vehicle 1c defined as the ordinary vehicle. In a case where the vehicle 1c defined as the ordinary vehicle is traveling in a manual drive mode, the control data generating unit 25 may generate control data to make notification of approach of the vehicles 1a and 1b defined as the emergency vehicles and the traveling directions of the vehicles 1a and 1b defined as the emergency vehicles, and send the control data to the vehicle 1c defined as the ordinary vehicle.

In a case where a plurality of vehicles (e.g., the vehicles 1a and 1b) are defined as the emergency vehicles, the control data generating unit 25 may sequentially receive the information on current positions of the vehicles 1 from the vehicles 1, generate the control data to allow the vehicle 1a defined as the emergency vehicle of high priority to travel preferentially over the vehicle 1b defined as the emergency vehicle of low priority, and send the control data to each of the vehicles 1 and/or the traffic light management device 30. For example, in a case where the vehicles 1a and 1b defined as the emergency vehicles are approaching an intersection at the same time, the control data generating unit 25 may generate a control signal to cause the traffic light 31a in front of the vehicle 1a defined as the emergency vehicle of high priority and traveling in an advancing direction to switch to green, and cause the traffic light 31b in front of the vehicle 1b defined as the emergency vehicle of low priority and traveling in an advancing direction to switch to red or yellow. The control data generating unit 25 may transmit the control signal to the traffic light management device 30.

Alternatively, the control data generating unit 25 may generate a control signal to accelerate or decelerate the vehicles 1a and 1b defined as the emergency vehicles, a control signal to change the traveling paths of the vehicles 1a and 1b defined as the emergency vehicles, or a control signal to change the traveling routes of the vehicles 1a and 1b defined as the emergency vehicles so that the vehicle 1a defined as the emergency vehicle of high priority passes through the intersection prior to the vehicle 1b defined as the emergency vehicle of low priority or so that the vehicle 1a defined as the emergency vehicle of high priority overtakes the vehicle 1b defined as the emergency vehicle of low priority. The control data generating unit 25 may then send the control signal to each of the vehicles 1a and 1b defined as the emergency vehicles. This allows the vehicle 1a defined as the emergency vehicle of high priority to travel preferentially over the other vehicles 1 while causing all the emergency vehicles (i.e., the vehicles 1a and 1b) to travel to the respective medical institutions 3 defined as the destinations smoothly.

[2. Example Operations]

The example configuration of the vehicle control system 100 according to an example embodiment of the technology is described above. Next, an operation of the vehicle control system 100 according to an example embodiment of the technology will now be described with reference to the flowcharts illustrated in FIGS. 3 to 6. In the example embodiment described below, the vehicles 1a and 1b may be defined as the emergency vehicles switched to the emergency mode, and the vehicle 1c may be defined as the ordinary vehicle not being switched to the emergency mode, as illustrated in the schematic diagram of FIG. 1. The medical institution 3A may be designated as a destination of the vehicle 1a defined as the emergency vehicle, and the medical institution 3B may be designated as a destination of the vehicle 1b defined as the other emergency vehicle. In the following description, some of the contents described above are not repeatedly described without a redundant description.

[2-1. Example Operations of Vehicle-Side Controller]

Figure 3:
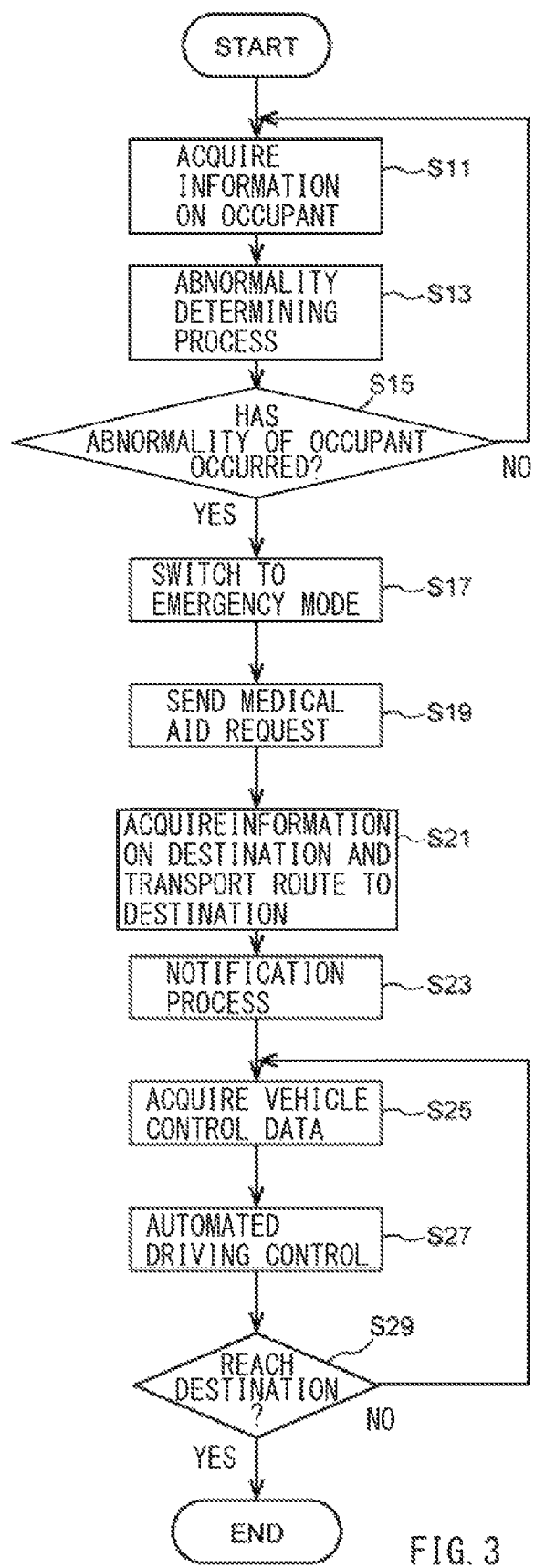
FIG. 3 is a flowchart illustrating an example operation of a vehicle controller according to one example embodiment of the technology.

FIG. 3 is a flowchart illustrating an example operation of the vehicle-side controller 50a mounted in the vehicle 1a. First, the occupant information acquiring unit 53 of the vehicle-side controller 50a may acquire information on the occupant of the vehicle 1a on the basis of the detection information received from the occupant detector 81 and the biological information detector 83 (Step S11). For example, the consciousness determining section 55 of the occupant information acquiring unit 53 may determine whether the occupant is unconscious on the basis of the image data of the occupant received from the occupant detector 81. Further, the biological information determining section 57 of the occupant information acquiring unit 53 may estimate biological information on one or more of the heart rate, pulse rate, blood pressure, breathing rate, blood glucose level, or brain waves of the occupant on the basis of the information received from the occupant detector 81 and/or the information received from the biological information detector 83. The biological information determining section 57 may correlate the estimated biological data with the attribution of the occupant and accumulate the resultant data on the database 60. In that case, the biological information determining section 57 may accumulate, in the database 60, information on whether the control mode is switched to the emergency mode together with the estimated biological information.

Thereafter, the emergency control unit 71 may determine the occurrence or absence of physical abnormality of the occupant on the basis of the information on the results of determination by the consciousness determining section 55 of the occupant information acquiring unit 53 and the information on the results of determination by the biological information determining section 57 of the occupant information acquiring unit 53 (Step S13). In Step S13, the emergency control unit 71 may also determine the degree of urgency of physical abnormality of the occupant.

Figure 4:
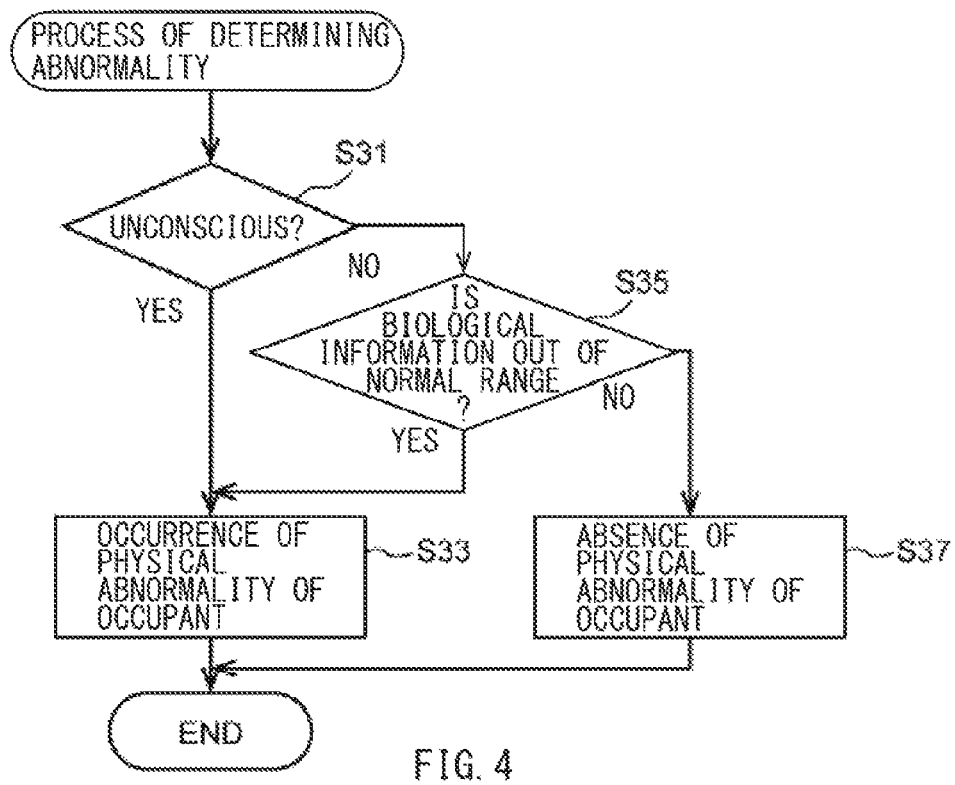
FIG. 4 is a flowchart illustrating an example process of determining the occurrence or absence of physical abnormality of an occupant.

FIG. 4 is a flowchart illustrating an example process of determining the occurrence or absence of physical abnormality of the occupant. The emergency mode setting section 73 of the emergency control unit 71 may determine whether the occupant is unconscious with reference to the results of determination by the consciousness determining section 55 (Step S31). If the occupant is unconscious (i.e., it is determined as "YES" in Step S31), the emergency mode setting section 73 may determine the occurrence of physical abnormality of the occupant (Step S33). In contrast, if the occupant is conscious (i.e., it is determined as "NO" in Step S31), the emergency mode setting section 73 may determine whether the detected biological information is out of the normal range with reference to the results of determination by the biological information determining section 57 and the normal range of the biological information of the occupant stored in the database 60 (Step S35).

If the detected biological information is out of the normal range (i.e., it is determined as "YES" in Step S35), the emergency mode setting section 73 may determine the occurrence of physical abnormality of the occupant (Step S33). In contrast, if the detected biological information falls within the normal range (i.e., it is determined as "NO" in Step S35), the emergency mode setting section 73 may determine the absence of physical abnormality of the occupant (Step S37).

Figure 5:
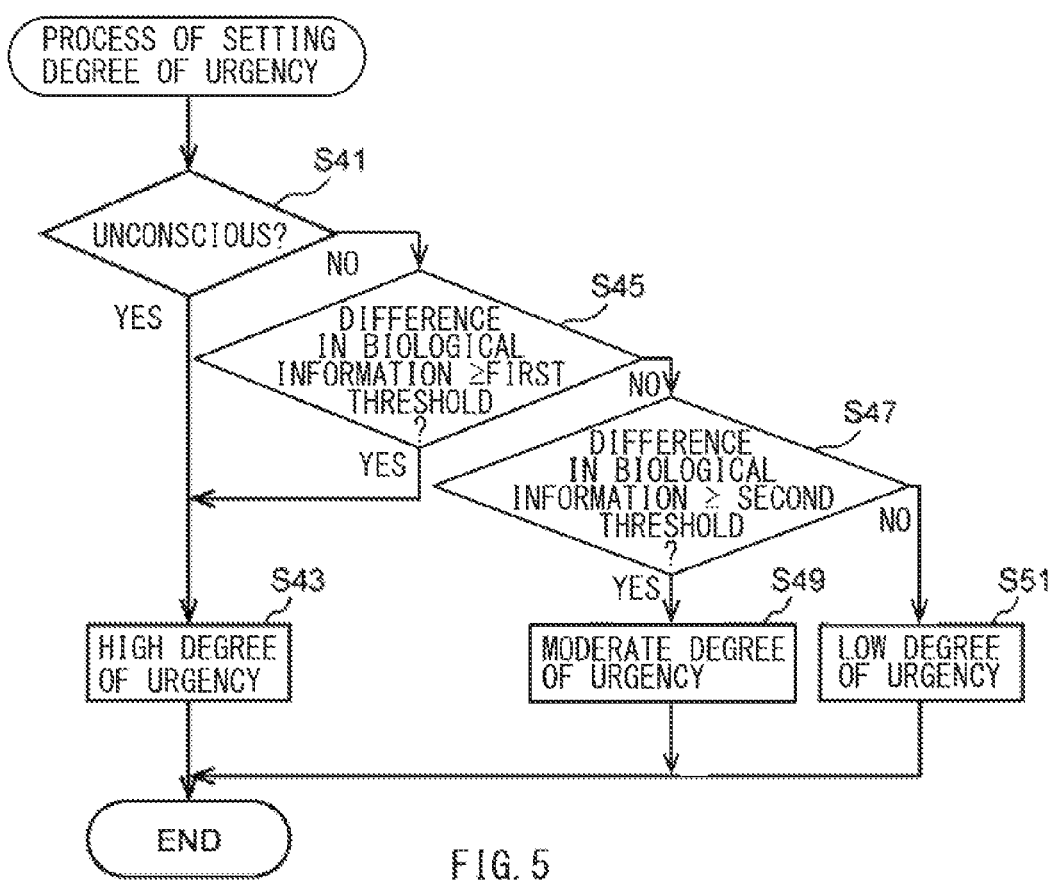
FIG. 5 is a flowchart illustrating an example process of determining the degree of urgency of physical abnormality of the occupant.

FIG. 5 is a flowchart illustrating an example process of determining the degree of urgency of physical abnormality of the occupant in the case of the occurrence of physical abnormality of the occupant. Note that the process of determining the degree of urgency should not be limited to the example described below.

If determining the occurrence of physical abnormality of the occupant (Step S33), the emergency mode setting section 73 may determine whether the occupant is unconscious (Step S41). If the occupant is unconscious (i.e., it is determined as "YES" in Step S41), the emergency mode setting section 73 may set a high degree of urgency (Step S43). If the occupant is conscious (i.e., it is determined as "NO" in Step S41), the emergency mode setting section 73 may determine whether the difference between the detected biological information and the normal range is equal to or greater than a first threshold set in advance (Step S45). For example, in a case where the pulse rate of the occupant is detected as the biological information, the first threshold may be 20. Note that, however, the first threshold may have any appropriate value.

If the difference is equal to or greater than the first threshold (i.e., it is determined as "YES" in Step S45), the emergency mode setting section 73 may set a high degree of urgency (Step S43). In contrast, if the difference is less than the first threshold (i.e., it is determined as "NO" in Step S45), the emergency mode setting section 73 may determine whether the difference between the detected biological information and the normal range is equal to or greater than a second threshold set in advance (Step 47). The second threshold may be less than the first threshold. In a case where the pulse rate of the occupant is detected as the biological information, the second predetermined threshold may be 10. Note that, however, the second threshold may have any appropriate value.

If the difference is equal to or greater than the second threshold (i.e., it is determined as "YES" in Step S47), the emergency mode setting section 73 may set a moderate degree of urgency (Step S49). In contrast, if it is determined as "NO" in Step S47, that is, if the detected biological information is out of the normal range and the difference is less than the second predetermined threshold, the emergency mode setting section 73 may set a low degree of urgency (Step S51).

Returning to FIG. 3, the emergency mode setting section 73 may determine whether a physical abnormality of the occupant has occurred (Step S15) through the determining process of Step S13. If no physical abnormality has occurred (i.e., it is determined as "NO" in Step S15), the process may return to Step S11 to repeat the determination as to whether a physical abnormality has occurred. In contrast, if a physical abnormality has occurred (i.e., it is determined as "YES" in Step S15), the emergency mode setting section 73 may switch the control mode of the vehicle 1a to the emergency mode (Step S17).

Thereafter, the emergency mode setting section 73 may send the medical aid request to the information processor 10 via the transmitter 67 (Step S19). The medical aid request may include the information on the physical condition of the occupant, such as the presence or absence of consciousness of the occupant or the biological information of the occupant, detected by the occupant information acquiring unit 53, the information on current position of the vehicle 1*a* detected by the position data acquiring unit 84, and the information on the degree of urgency. Optionally, the medical aid request may include the information on chronic diseases and medical history of the occupant retrieved from the database 60. As described below with reference to an example flowchart, the information processor 10 may designate the medical institution 3A as the destination of the vehicle 1*a*, and transmit the information on the destination together with the information on the transport route to the destination to the vehicle-side controller 50*a*.

Thereafter, the route setting section 75 of the emergency control unit 71 may acquire the information on the medical institution 3A designated as the destination by the information processor 10 and the information on the transport route to the destination via the receiver 69 (Step S21). On the basis of the information acquired, the route setting section 75 may designate the medical institution 3A as the destination and set the transport route to the destination as the traveling route.

Thereafter, the notification control unit 79 may perform control to cause the notification unit 89 to make predetermined notification (Step S23). The notification control unit 79 may cause the notification unit 89 to make notification of at least the control mode of the vehicle 1*a* being set to the emergency mode and the medical institution 3A being designated as the destination. In addition to such notification, the notification control unit 79 may cause the notification unit 89 to make notification of at least one of the scheduled arrival time to the medical institution 3A, the traveling route to the medical institution 3A, or the order of priority of the vehicle 1*a*.

Thereafter, the emergency control unit 71 may acquire the control data for the vehicle 1*a* generated by the information processor 10 via the receiver 69 (Step S25). The control data for the vehicle 1*a* acquired may include information on the order of priority of the own vehicle (i.e., the vehicle 1*a*) between the vehicles 1*a* and 1*b* defined as the emergency vehicles, control data to accelerate, decelerate, or stop the own vehicle (i.e., the vehicle 1*a*), control data to change the traveling path or the traveling route of the own vehicle (i.e., the vehicle 1*a*). When receiving the control data for the vehicle 1*a*, the notification control unit 79 may cause the notification unit 89 to make notification of at least part of the acquired control data.

Thereafter, the automated driving control unit 77 may perform the automated driving control that causes the vehicle 1*a* to travel along the set traveling route to the medical institution 3A designated as the destination (Step S27). For example, the automated driving control unit 77 may generate a control signal to be sent to the vehicle drive control unit 87 on the basis of the information on current position of the vehicle 1*a* received from the position data acquiring unit 84, the information on surrounding environment of the vehicle 1*a* received from the surrounding environment detector 85, and the information on the destination and the traveling route set by the route setting section 75.

For example, the automated driving control unit 77 may set target values of the steering angle, vehicle speed, acceleration rate, and braking force of the vehicle 1*a* to cause the vehicle 1*a* to travel avoiding a contact with other vehicles, persons, or obstacles present around the vehicle 1*a* along the traveling route. The automated driving control unit 77 may transmit the target values to the vehicle drive control unit 87. During the automated driving control, the emergency control unit 71 may sequentially transmit the information on current position of the vehicle 1*a* to the information processor 10. Further, the automated driving control unit 77 may set a target value of the control by the vehicle drive control unit 87 on the basis of the control data for the vehicle 1*a* sequentially transmitted from the information processor 10. The vehicle drive control unit 87 may receive a control signal to control the steering control system, the engine, the drive motor, the brake system or the like so that the vehicle 1*a* is caused to travel to the medical institution 3A.

Thereafter, the automated driving control unit 77 may determine whether the vehicle 1*a* has reached the medical institution 3A designated as the destination (Step S29). If the vehicle 1*a* has not been reached the medical institution 3A yet (i.e., it is determined as "NO" in Step S29), the process may return to Step S25 in which the automated driving control unit 77 continues to perform the automated driving control. In contrast, if the vehicle 1*a* has reached the medical institution 3A (i.e., it is determined as "YES" in Step S29), the automated driving control unit 77 may stop the automated driving control to terminate the series of control processes.

Likewise, the vehicle-side controller 50*b* mounted in the vehicle 1*b* defined as the other emergency vehicle may designate the medical institution 3B, which has been set as the destination by the information processor 10, as the destination, and set, as the traveling route, the transport route set by the information processor 10 to perform the automated driving control. The vehicle-side controller 50*c* mounted in the vehicle 1*c* defined as the ordinary vehicle may cause the vehicle 1*c* to travel under the automated driving control to an appropriate destination without switching the control mode of the vehicle 1*c* to the emergency mode, for example. The vehicle-side controller 50*b* may sequentially transmit the information on current position of the vehicle 1*b* to the information processor 10. When receiving the control data for the vehicle 1*b* from the information processor 10, the vehicle-side controller 50*b* may control the vehicle drive control unit 87 on the basis of the control data. The vehicle-side controller 50*c* may sequentially transmit the information on current position of the vehicle c to the information processor 10. When receiving the control data for the vehicle 1*c* from the information processor, the vehicle-side controller 50*c* may control the vehicle drive control unit 87 on the basis of the control data.

[2-2. Example Operations of Information Processor]

Figure 6:
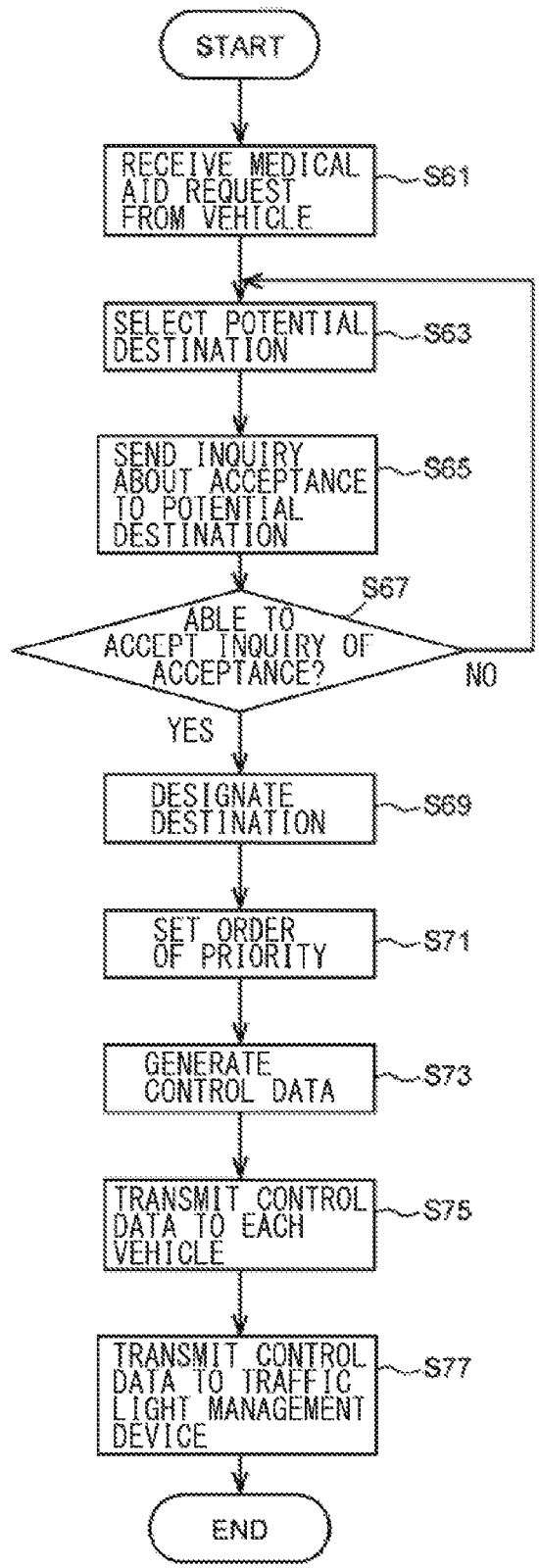
FIG. 6 is a flowchart illustrating an example operation of an information processor according to one example embodiment of the technology.

FIG. 6 is a flowchart illustrating an example operation of the information processor 10.

First, the medical aid controller 20 in the information processor 10 may receive the medical aid request sent from the vehicle 1*a* switched to the emergency mode (Step S61). Next, with reference to the database 29, the destination setting unit 21 in the medical aid controller 20 may select any of the medical institutions 3 as a potential destination of the vehicle 1*a* defined as the emergency vehicle on the basis of the medical aid request received from the vehicle 1*a* defined as the emergency vehicle (Step S63). For example, the destination setting unit 21 may select, as a potential destination, any of the medical institutions 3 that is able to offer a medical service to the occupant on the basis of the information on current position of the vehicle 1*a* defined as the emergency vehicle and the information on chronic diseases and medical history of the occupant estimated to have a physical abnormality.

Thereafter, the destination setting unit 21 may send the inquiry about acceptance to the medical institution 3 selected as the potential destination via the third communication unit 19 (Step S65). In Step S65, the destination setting unit 21 may send the biological information of the occupant estimated to have a physical abnormality, the information on the degree of urgency of physical abnormality, and the information on current position of the vehicle 1a together with the inquiry about acceptance.

Figure 7:
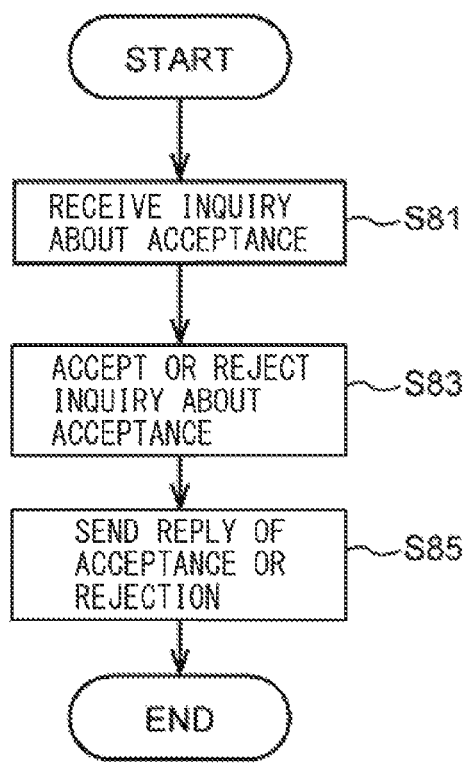
FIG. 7 is a flowchart illustrating an example process executed by a system of a medical institution in response to an inquiry about acceptance.

FIG. 7 is a flowchart illustrating a process executed by a system of the medical institution 3 in response to the inquiry about acceptance. When receiving the inquiry about acceptance (Step S81), the system of the medical institution 3 may accept or reject the inquiry (Step S83). The acceptance or rejection of the inquiry may be set through an input operation by an operator in the medical institution 3 or the system on the basis of information on attendance rate of doctors or status of emergency treatment for other patients, for example. When the inquiry about acceptance is accepted or rejected, the system of the medical institution 3 may send the information on the acceptance or rejection of the inquiry to the information processor 10 (Step S85).

Returning to FIG. 6, the destination setting unit 21 may determine whether the medical institution 3 selected as the potential destination is able to accept the inquiry on the basis of the reply of acceptance or rejection received (Step S67). If the inquiry about acceptance is rejected (i.e., it is determined as "NO" in Step S67), the process may return to Step S63 in which the destination setting unit 21 may repeat the determination as to whether another medical institution 3 selected as the potential destination is able to accept the inquiry. In contrast, if the inquiry about acceptance is accepted (i.e., it is determined as "YES" in Step S67), the destination setting unit 21 may designate the medical institution 3A sending a reply of acceptance as the destination (Step S69).

The destination setting unit 21 may also designate the medical institution 3B as the destination of the vehicle 1b defined as the other emergency vehicle through Steps S61 to S69 described above.

Thereafter, the priority setting unit 23 in the medical aid controller 20 may set the order of priority between the vehicles 1a and 1b defined as the emergency vehicles switched to the emergency mode (Step S71). The medical aid request sent from each of the vehicles 1a and 1b defined as the emergency vehicles may include the information on the degree of urgency of physical abnormality of the occupant. The priority setting unit 23 may set a higher priority to the vehicle 1a or 1b defined as the emergency vehicle, whichever is of a higher degree of urgency. In a case where the same degree of urgency is set to a plurality of vehicles, the priority setting unit 23 may set the order of priority between the vehicles 1a and 1b defined as the emergency vehicles on the basis of the chronic diseases or the medical history of the occupant included in the medical aid request. The order of priority based on the chronic diseases and the medical history may be stored in the database 29 in advance.

Thereafter, the control data generating unit 25 may generate control data to control the vehicles 1a and 1b defined as the emergency vehicles, the vehicle 1c defined as the ordinary vehicle, and the traffic light management device 30 on the basis of the information on the medical institution 3 designated as the destination by the destination setting unit 21, the information on the transport route to the medical institution 3, the order of priority between the vehicles 1a and 1b defined as the emergency vehicles and set by the priority setting unit 23, the medical aid requests sent from the vehicle-side controllers 50a and 50b, and the information on positions of the vehicles 1a to 1c (Step S73).

In the example illustrated in FIG. 1, the control data generating unit 25 may generate control data that causes the vehicle 1c defined as the ordinary vehicle to decelerate or move to a side of the road to allow the vehicle 1a defined as the emergency vehicle to overtake the vehicle 1c defined as the ordinary vehicle. Further, the control data generating unit 25 may generate control data that causes the vehicle 1c defined as the ordinary vehicle to decelerate so as not to enter the intersection 7 prior to the vehicle 1b defined as the other emergency vehicle. Further, the control data generating unit 25 may generate control data that causes the vehicle 1b defined as the emergency vehicle of low priority to decelerate so that the vehicle 1a defined as the emergency vehicle of high priority passes through the intersection 7 prior to the vehicle 1b defined as the emergency vehicle of low priority. Further, the control data generating unit 25 may generate a control signal to control the traffic light management device 30. On the basis of the control signal, the traffic light management device 30 may cause the traffic light 31a in front of the vehicle 1a defined as the emergency vehicle of high priority and traveling in an advancing direction to switch to green, and cause the traffic light 31b in front of the vehicle 1b defined as the emergency vehicle of low priority and traveling in an advancing direction to switch to red so that the vehicle 1a defined as the emergency vehicle of high priority passes through the intersection 7 prior to the vehicle 1b defined as the emergency vehicle of low priority.

The control data generating unit 25 may transmit the generated control data for the vehicles 1a to 1c to the respective vehicles 1a to 1c via the first communication unit 11 (Step S75). The control data generating unit 25 may transmit the generated control data for the traffic lights 31 to the traffic light management device 30 via the second communication unit 17 (Step S77). This allows the vehicle 1a defined as the emergency vehicle of high priority to travel on a top-priority basis while causing all the emergency vehicles (i.e., the vehicles 1a and 1b) to the respective medical institutions 3A and 3B designated as the destinations preferentially over the vehicle 1c defined as the ordinary vehicle.

According to the vehicle control system 100 of the example embodiment described above, the vehicle-side controller 50 may switch the control mode of the own vehicle (i.e., the vehicle 1a) to the emergency mode when detecting a physical abnormality of the occupant, and send the medial aid request to the information processor 10. When receiving the medical aid request, the information processor 10 may designate any of the medical institutions 3 as the destination of the vehicle 1a switched to the emergency mode, set the transport route to the medical institution 3, send the information on the medical institution 3 designated as the destination and the information on the transport route to the medical institution 3 to the vehicle 1a defined as the emergency vehicle, generate the control signal to control the other vehicles and the traffic lights 31 so that the vehicle 1a defined as the emergency vehicle is allowed to travel preferentially over the other vehicles, and send the generated control signal to the other vehicles and the traffic light management device 30. In a case where a plurality of vehicles (e.g., the vehicles 1a and 1b) are defined as the emergency vehicles, the information processor 10 may set the order of priority between the vehicles 1a and 1b defined as the emergency vehicles on the basis of the information on physical abnormality of the occupant of each of the vehicles 1a and 1b defined as the emergency vehicles so that the vehicle 1a defined as the emergency vehicle of high priority is allowed to travel preferentially over the vehicle 1b defined as the emergency vehicle of low priority. This allows the vehicle 1a defined as the emergency vehicle of high priority to travel preferentially over the vehicle 1b defined as the emergency vehicle of low priority while causing all the emergency vehicles (i.e., the vehicles 1a and 1b) to the respective medical institutions 3 designated as the destinations smoothly.

Further, the information processor 10 of the vehicle control system 100 according to the example embodiment may designate the medical institutions 3 as the destination when receiving the medical aid request from the vehicles 1a and 1b defined as the emergency vehicles. Accordingly, the vehicles 1a and 1b defined as the emergency vehicles are caused to travel to the respective medical institutions 3 designated as an appropriate destinations even if the occupant is unconscious or unable to make a driving operation or a response in a normal way.

Second Example Embodiment

Now described is an example configuration of a vehicle control system according to a second example embodiment of the technology. In the first example embodiment described above, the vehicle control system may include the vehicle-side controller mounted in each of the vehicles 1 and the information processor. However, in the second example embodiment, the information processor may be omitted, and the vehicle-side controller mounted in each of the vehicles 1 may also serve as the information processor. The following description focuses on a difference between the vehicle controller according to the first example embodiment and the vehicle controller according to the second example embodiment.

Figure 8:
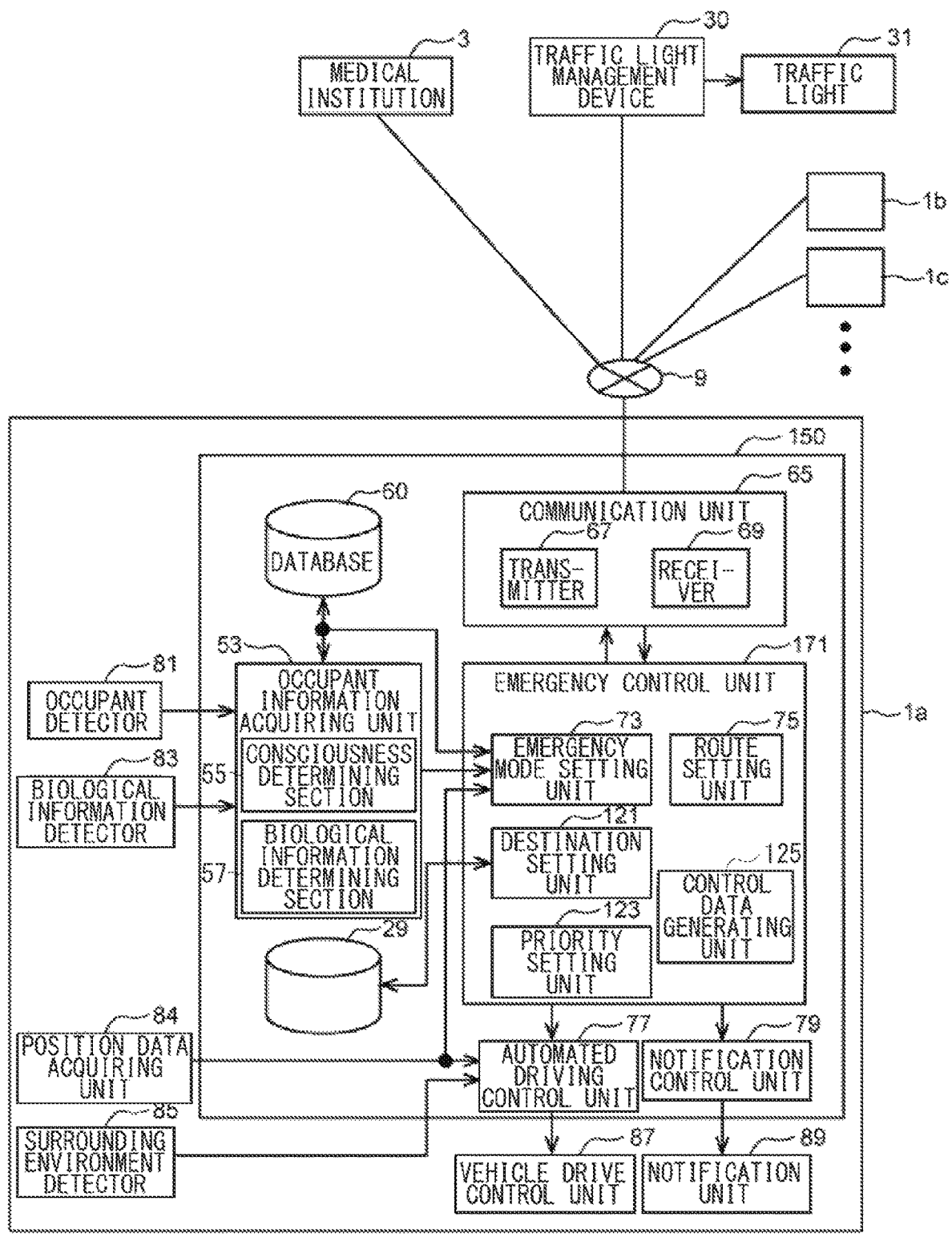
FIG. 8 is a block diagram illustrating an example configuration of a vehicle controller according to one example embodiment of the technology.

FIG. 8 is a block diagram illustrating an example configuration of a vehicle controller 150 according to the second example embodiment. The vehicle controller 150 may differ from the vehicle-side controller 50 according to the first example embodiment in that the emergency control unit 171 of the vehicle controller 150 includes the destination setting unit 121, the priority setting unit 123, and the control data generating unit 25, and that the vehicle-side controller 50 includes the database 29 that stores the data on the medical institutions 3. The vehicle controller 150 may be configured to communicate with the medical institutions 3 and the traffic light management device 30 via the mobile communication network 9, for example.

The operations of the destination setting unit 121, the priority setting unit 123, and the control data generating unit 25 in the emergency control unit 171 may be the same as those of the destination setting unit 21, the priority setting unit 23, and the control data generating unit 25 in the information processor 10 according to the first example embodiment. However, unlike the first example embodiment, the destination setting unit 121 according to the second example embodiment may designate any of the medical institutions 3 as the destination of the own vehicle (i.e., the vehicle 1a) but does not designate the destinations of the other vehicles 1b and 1c. Further, the emergency control unit 171 according to the second example embodiment may receive other vehicle information from the vehicle 1b defined as the other emergency vehicle via the receiver 69. The other vehicle information on the vehicle 1b may include the information on the medical aid request. The emergency control unit 171 may further receive other vehicle information from the vehicle 1c defined as the ordinary vehicle. The other vehicle information on the vehicle 1c may include the information on current position of the vehicle 1c defined as the ordinary vehicle. The medical aid request received from the vehicle 1b defined as the other emergency vehicle may include the information on current position of the vehicle 1b defined as the other emergency vehicle, the information on the destination designated, the biological information of the occupant of the vehicle 1b defined as the other emergency vehicle, and the information on the degree of urgency of physical abnormality of the occupant.

The priority setting unit 123 according to the second example embodiment may set the order of priority between the vehicles 1a and 1b defined as the emergency vehicles on the basis of the information on the physical condition of the occupant of the own vehicle (i.e., the vehicle 1a), the information on the degree of urgency of physical abnormality of the occupant of the own vehicle (i.e., the vehicle 1a), the information on the physical condition of the occupant of the vehicle 1b defined as the other emergency vehicle, and the information on the degree of urgency of physical abnormality of the occupant of the vehicle 1b defined as the other emergency vehicle. The priority setting unit 123 according to the second example embodiment may set the order of priority in a similar way to the priority setting unit 23 of the information processor 10 according to the first example embodiment. The control data generating unit 25 may generate control data for the vehicles 1a and 1b defined as the emergency vehicles, the vehicle 1c defined as the ordinary vehicle, and the traffic light management device 30 on the basis of the information on the medical institutions 3 designated as the destinations of the vehicles 1a and 1b defined as the emergency vehicles, the transport routes to the medical institutions 3, and the order of priority set by the priority setting unit 123 between the vehicles 1a and 1b defined as the emergency vehicles. The control data generating unit 25 may send the generated control data to the vehicle 1b defined as the other emergency vehicle, the vehicle 1c defined as the ordinary vehicle, and the traffic light management device 30 via the transmitter 67.

The components other than ones described in the second example embodiment may be the same as the corresponding components in the vehicle control system 100 according to the first example embodiment.

According to the second example embodiment, the vehicle controller 150 may, if determining the occurrence of physical abnormality of the occupant, switch the control mode of the own vehicle (i.e., the vehicle 1a) to the emergency mode, designate any of the medical institutions 3 as the destination, set the transport route to the designated medical institution 3, generate the control signal so that the other vehicles and the traffic lights 31 are controlled to allow the vehicle 1a defined as the emergency vehicle to travel preferentially over the other vehicles, and send the control signal to the other vehicles and the traffic light management device 30. In a case where a plurality of vehicles (e.g., the vehicles 1a and 1b) are defined as the emergency vehicles, the emergency control unit 171 may set the order of priority between the vehicles 1a and 1b defined as the emergency vehicles on the basis of the information on physical abnormality of the occupant of each of the vehicles 1a and 1b defined as the emergency vehicles, and generate the control signal so that the vehicle 1a defined as the emergency vehicle of high priority is allowed to travel preferentially over the vehicle 1b defined as the emergency vehicle of low priority. This allows the vehicle 1a defined as the emergency vehicle of high priority to travel preferentially over the vehicle 1b defined as the emergency vehicle of low priority while causing all the emergency vehicles (i.e., the vehicles 1a and 1b) to travel to the respective medical institutions 3 defined as the destinations smoothly.

Further, in a case where the control mode of the own vehicle (i.e., the vehicle 1a) is switched to the emergency mode, the vehicle controller 150 according to the second example embodiment may designate any of the medical institutions 3 as the destination by communicating with the medical institution 3. Accordingly, the vehicle 1a defined as the emergency vehicle is caused to travel to the medical institution 3 designated as an appropriate destination even if the occupant is unconscious or unable to make a driving operation or a response in a normal way.

Some example embodiments of the technology are described in detail above with reference to the accompanying drawings. It should be appreciated that the example embodiments of the technology described above are mere examples and are not intended to limit the scope of the technology. It should be also appreciated that various omissions, replacements, and modifications may be made in the foregoing example embodiments described herein, without departing from the scope of the technology. The technology is intended to include such modifications and alterations in so far as they fall within the scope of the appended claims or the equivalents thereof.

For example, although the vehicles 1a to 1c are driven under the automated driving control in the foregoing example embodiments, these example embodiments are non-limiting examples of the technology. In another example embodiment, the vehicle 1c defined as the ordinary vehicle may be driven only in a manual mode. In such an example embodiment, when receiving a control signal that causes the vehicle 1c to decelerate or stop or a control signal that changes the traveling path or route of the vehicle 1c, the vehicle-side controller 50c mounted in the vehicle 1c may perform only the control to notify the driver of the vehicle 1c of the deceleration or stop or the change in the traveling path or route. Even in such a case, the driver receiving the notification is able to perform a driving operation of the vehicle 1c so that the vehicles 1a and 1b defined as the emergency vehicles are allowed to travel preferentially over the other vehicles.

One or more of the emergency mode setting section 73 and the transmitter 67 in the vehicle-side controller 50a and the control data generating unit 25 and the transmitter 13 in the information processor 10 illustrated in FIG. 2 are implementable by circuitry including at least one semiconductor integrated circuit such as at least one processor (e.g., a central processing unit (CPU)), at least one application specific integrated circuit (ASIC), and/or at least one field programmable gate array (FPGA). At least one processor is configurable, by reading instructions from at least one machine readable non-transitory tangible medium, to perform all or a part of functions of the emergency mode setting section 73, the transmitter 67, the control data generating unit 25, and the control data transmitter 13. Such a medium may take many forms, including, but not limited to, any type of magnetic medium such as a hard disk, any type of optical medium such as a CD and a DVD, any type of semiconductor memory (i.e., semiconductor circuit) such as a volatile memory and a non-volatile memory. The volatile memory may include a DRAM and a SRAM, and the nonvolatile memory may include a ROM and an NVRAM.

The ASIC is an integrated circuit (IC) customized to perform, and the FPGA is an integrated circuit designed to be configured after manufacturing in order to perform, all or a part of the functions of the emergency mode setting section 73, the transmitter 67, the control data generating unit 25, and the control data transmitter 13 illustrated in FIG. 2.

The invention claimed is:

1. A vehicle controller comprising
a processor configured to
switch, when detecting a physical abnormality of an occupant of an own vehicle on a basis of physical information of the occupant of the own vehicle, the own vehicle to an emergency mode in which the own vehicle is caused to automatically travel to a predetermined destination,
receive, in a case where the own vehicle is switched to the emergency mode, other vehicle information from another vehicle switched to the emergency mode together with the own vehicle, the other vehicle information including at least information on a physical abnormality of an occupant of the other vehicle,
set, on a basis of the other vehicle information received and own vehicle information including information on the physical abnormality of the occupant of the own vehicle, an order of priority between the own vehicle and the other vehicle to determine which of the own vehicle or the other vehicle is allowed to travel, and
send a medical aid request to an information processor on a basis of the order of priority set, the information processor being configured to output control data to the other vehicle and a traffic light.

2. The vehicle controller according to claim 1, wherein the processor is configured to determine the physical abnormality of the occupant of the own vehicle on a basis of at least one of the physical information of the occupant of the own vehicle as to whether the occupant of the own vehicle is unconscious or biological information of the occupant of the own vehicle.

3. The vehicle controller according to claim 2, wherein the processor is configured to
set a degree of urgency of the physical abnormality of the occupant of the own vehicle on a basis of the physical information of the occupant of the own vehicle, and
send an inquiry about acceptance to a plurality of medical institutions, the inquiry about acceptance including information on a current position of the own vehicle and information on the degree of urgency, the plurality of medical institutions being located within a predetermined range from the current position of the own vehicle.

4. The vehicle controller according to claim 3, wherein, when receiving a reply of acceptance from any of the plurality of medical institutions to which the inquiry about acceptance has been sent, the processor is configured to designate a medical institution as a destination to which the occupant of the own vehicle is to be transported.

5. The vehicle controller according to claim 1, wherein the processor is configured to
set a degree of urgency of the physical abnormality of the occupant of the own vehicle on a basis of the physical information of the occupant of the own vehicle, and
send an inquiry about acceptance to a plurality of medical institutions, the inquiry about acceptance including information on a current position of the own vehicle and information on the degree of urgency, the plurality of medical institutions being located within a predetermined range from the current position of the own vehicle.

6. The vehicle controller according to claim 5, wherein, when receiving a reply of acceptance from any of the plurality of medical institutions to which the inquiry about acceptance has been sent, the processor is configured to designate a medical institution as a destination to which the occupant of the own vehicle is to be transported.

7. The vehicle controller according to claim 5, wherein the processor is configured to
set a destination to which the occupant of the own vehicle is to be transported and a transport route to the destination, and
transmit, to a traffic light management device, the information on the degree of urgency, information on the destination, and information on the transport route.

8. The vehicle controller according to claim 7, wherein, when receiving a reply of acceptance from any of the plurality of medical institutions to which the inquiry about acceptance has been sent, the processor is configured to designate the medical institution as a destination to which the occupant of the own vehicle is to be transported.

9. A vehicle control system comprising:
a vehicle-side controller configured to control an own vehicle; and
an information processor configured to transmit control data to the own vehicle, another vehicle, and a traffic light management device, wherein
the vehicle-side controller includes:
  vehicle-side circuitry configured to switch, when detecting a physical abnormality of an occupant of the own vehicle on a basis of physical information of the occupant of the own vehicle, the own vehicle to an emergency mode in which the own vehicle is caused to automatically travel to a predetermined destination, and
  a transmitter configured to send a medical aid request to the information processor in a case where the own vehicle is switched to the emergency mode, the medical aid request including information on the physical abnormality of the occupant of the own vehicle and requesting the information processor to control the other vehicle and a traffic light to allow the own vehicle to travel, and
the information processor includes
  information circuitry configured to generate control data for the own vehicle, the other vehicle, and the traffic light management device on a basis of the medical aid request, and
  a control data transmitter configured to transmit the control data for the own vehicle, the other vehicle, and the traffic light management device to the own vehicle, the other vehicle, and the traffic light management device, wherein,
  in a case where the other vehicle is switched to the emergency mode together with the own vehicle, the information circuitry is configured to generate the control data for the own vehicle, the other vehicle, and the traffic light management device on a basis of the information on the physical abnormality of the occupant of the own vehicle switched to the emergency mode and information on a physical abnormality of an occupant of the other vehicle switched to the emergency mode, to allow either one of the own vehicle and the other vehicle to travel.

10. The vehicle control system according to claim 9, wherein
the information processor is further configured to set, in a case where the other vehicle is switched to the emergency mode together with the own vehicle, an order of priority between the own vehicle and the other vehicle to determine which of the own vehicle or the other vehicle is allowed to travel on a basis of the information on the physical abnormality of the occupant of the own vehicle received from the own vehicle and the information on the physical abnormality of the occupant of the other vehicle received from the other vehicle, and
the information circuitry is configured to generate the control data for the own vehicle, the other vehicle, and the traffic light management device on a basis of information on the order of priority.

11. The vehicle control system according to claim 10, wherein
the vehicle-side circuitry of the vehicle-side controller is configured to set a degree of urgency of the physical abnormality of the occupant of the own vehicle on a basis of the physical information of the occupant of the own vehicle,
the transmitter of the vehicle-side controller is configured to transmit, to the information processor, information on a current position of the own vehicle and information on the degree of urgency, and
the information processor is configured to send an inquiry about acceptance to a plurality of medical institutions, the inquiry about acceptance including the information on the current position of the own vehicle and the information on the degree of urgency, the plurality of medical institutions being located within a predetermined range from the current position of the own vehicle.

12. The vehicle control system according to claim 11, wherein,
when receiving a reply of acceptance from any of the plurality of medical institutions to which the inquiry about acceptance has been sent, the information processor is configured to designate the medical institution as a destination to which the occupant of the own vehicle is to be transported.

13. The vehicle control system according to claim 10, wherein
the information processor is configured to set a destination to which the occupant of the own vehicle is to be transported and a transport route to the destination, and
the information circuitry is configured to generate the control data for the own vehicle, the other vehicle, and the traffic light management device on a basis of information on the vehicle allowed to travel, information on the destination, and information on the transport route to the destination.

14. The vehicle control system according to claim 9, wherein
the vehicle-side circuitry of the vehicle-side controller is configured to set a degree of urgency of the physical abnormality of the occupant of the own vehicle on a basis of the physical information of the occupant of the own vehicle,
the transmitter of the vehicle-side controller is configured to transmit, to the information processor, information on a current position of the own vehicle and information on the degree of urgency, and the information processor is configured to send an inquiry about acceptance to a plurality of medical institutions, the inquiry about acceptance including the information on the current position of the own vehicle and the information on the degree of urgency, the plurality of medical institutions being located within a predetermined range from the current position of the own vehicle.

15. The vehicle control system according to claim 14, wherein, when receiving a reply of acceptance from any of the plurality of medical institutions to which the inquiry about acceptance has been sent, the information processor is configured to designate the medical institution as a destination to which the occupant of the own vehicle is to be transported.

16. The vehicle control system according to claim 9, wherein the information processor is configured to set a destination to which the occupant of the own vehicle is to be transported and a transport route to the destination, and the information circuitry is configured to generate the control data for the own vehicle, the other vehicle, and the traffic light management device on a basis of information on the vehicle allowed to travel, information on the destination, and information on the transport route to the destination.

17. A vehicle control system comprising:

a vehicle-side controller configured to control an own vehicle; and an information processor configured to transmit control data to the own vehicle, other vehicle, and a traffic light management device, wherein the vehicle-side controller includes circuitry configured to switch, when detecting a physical abnormality of an occupant of the own vehicle on a basis of physical information of the occupant of the own vehicle, the own vehicle to an emergency mode in which the own vehicle is caused to automatically travel to a predetermined destination, and send a medical aid request to the information processor in a case where the own vehicle is switched to the emergency mode, the medical aid request including information on the physical abnormality of the occupant of the own vehicle and requesting the information processor to control the other vehicle and a traffic light to allow the own vehicle to travel, and the information processor includes circuitry configured to generate control data for the own vehicle, the other vehicle, and the traffic light management device on a basis of the medical aid request, and transmit the control data for the own vehicle, the other vehicle, and the traffic light management device to the own vehicle, the other vehicle, and the traffic light management device, wherein, in a case where the other vehicle is switched to the emergency mode together with the own vehicle, the circuitry is configured to generate the control data for the own vehicle, the other vehicle, and the traffic light management device on a basis of the information on the physical abnormality of the occupant of the own vehicle switched to the emergency mode and information on a physical abnormality of an occupant of the other vehicle switched to the emergency mode, to allow either one of the own vehicle and the other vehicle to travel.

* * * * *